US008981087B2

(12) United States Patent
Shuttleworth et al.

(10) Patent No.: US 8,981,087 B2
(45) Date of Patent: Mar. 17, 2015

(54) BENZO [E] [1,3] OXAZIN-4-ONE DERIVATIVES AS PHOSPHOINOSITIDE 3-KINASE INHIBITORS

(75) Inventors: Stephen Joseph Shuttleworth, Southampton (GB); Franck Alexandre Silva, Southampton (GB); Alexander Richard Liam Cecil, Southampton (GB); Thomas James Hill, Southampton (GA)

(73) Assignee: Karus Therapeutics Limited, Hampshire (GB)

( * ) Notice: Subject to any disclaimer, the term of this patent is extended or adjusted under 35 U.S.C. 154(b) by 149 days.

(21) Appl. No.: 13/384,310

(22) PCT Filed: Jul. 23, 2010

(86) PCT No.: PCT/GB2010/051221
§ 371 (c)(1),
(2), (4) Date: Feb. 6, 2012

(87) PCT Pub. No.: WO2011/012883
PCT Pub. Date: Feb. 3, 2011

(65) Prior Publication Data
US 2012/0129848 A1    May 24, 2012

(30) Foreign Application Priority Data

Jul. 29, 2009  (GB) .................................. 0913248.1
Sep. 9, 2009   (GB) .................................. 0915789.2

(51) Int. Cl.
C07D 265/24    (2006.01)
C07D 413/04    (2006.01)
A61K 31/536    (2006.01)
A61K 31/5365   (2006.01)
A61P 19/02     (2006.01)

(52) U.S. Cl.
CPC ..................................... C07D 265/24 (2013.01)
USPC ...... 544/92; 540/488; 514/230.5; 514/211.01

(58) Field of Classification Search
USPC .............. 544/92; 540/488; 514/230.5, 211.01
See application file for complete search history.

(56) References Cited

U.S. PATENT DOCUMENTS 3,491,092 A * 1/1970 Grigat et al. .................... 544/73
5,703,075 A   12/1997 Gammill et al.
7,361,662 B2  4/2008 Rault et al.

FOREIGN PATENT DOCUMENTS

WO  WO 2004/043956  5/2004

OTHER PUBLICATIONS

Cecil Textbook of Medicine, edited by Bennet, J.C., and Plum F., 20th edition,vol. 1, 1004-101 O, 1996.*
Mass, R. D., Int. J. Radiation Oncology Bio. Phys.vol. 58(3): 932-940, 2004.*
Fabbro et al. Pharmacology & therapeutics 93, 79-98, 2002.*
Cohen et al., Current Opinion in Chemical Biology, 3,459-465, 1999.*
Freshney et al.,Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Ameriks et al., "Small Molecule Inhibitors of Phosphoinositide 3-Kinase (PI3K) δ and γ", *Current Topics in Medicinal Chemistry*, 2009, vol. 9, No. 8, pp. 738-753.
Verheijen et al., "Phosphatidylinositol 3-kinase (PI3K) inhibitors as anticancer drugs", *Drugs of the Future*, 2007, vol. 32, No. 6, pp. 537-547.

* cited by examiner

*Primary Examiner* — Venkataraman Balasubramanian
(74) *Attorney, Agent, or Firm* — Saliwanchik, Lloyd & Eisenschenk

(57) ABSTRACT

Compounds of formula (I): wherein: W is O, N—H, N-alkyl, N-alkenyl, N-alkynyl, N-aryl, N-heteroaryl or S; each X is independently CH or N; $R^1$ is formula (b) or $R^3$ is H, alkyl, $NH_2$, OH, =O or halogen; each A and B are independently CH or N; D is $NHR_4$; $R^4$ is H, alkyl, —C(O)-alkyl. —C(O)—$NH_2$, —C(O)—NH-alkyl, —$SO_2$-alkyl, —$SO_2$—$NH_2$ or —$SO_2$—NH-alkyl; $R^2$ is aryl substituted with at least one nitrogen-containing group or $R^2$ is a nitrogen-containing heteroaryl, cycloalkyl substituted with a nitrogen-containing group, nitrogen-containing cycloalkyl, $C_1$-$C_6$ mono alkylamino, $C_1C_6$ bis alkylamino, $C_1C_6$ acylamino, $C_1$-$C_6$ aminoalkyl, mono ($C_1C_6$ alkyl)amino $C_1$-$C_6$ alkyl, bis ($C_1C_6$ alkyl)amino $C_1C_6$ alkyl, $C_1$-$C_6$-acylamino or $C_1$ $C_6$ alkynyl-$NR^{11}$, $R^{11}$ is H, alkyl, alkenyl, alkynyl, aryl, heteroaryl, halogen, O-alkyl, NH-alkyl, N-dialkyl, —C(O)—$R^7$, —C(O)—$NH_2$, —C(O)—NH—$R^7$, —$SO_2$—$R^7$, —$SO_2$—$NH_2$, —$SO_2$—NH—$R^7$, NH-acyl, NH-sulfonyl, $NR^7$-acyl, $NR^7$-sulfonyl, N—C(O)—NH—$R^7$, N—$SO_2$—NH—$R^7$, N—C(O)—$NR^7R^7$ or N—$SO_2$—$NR^7R^7$; and $R^7$ is alkyl, aryl or heteroaryl, are useful as PI3K inhibitors and are useful in therapy.

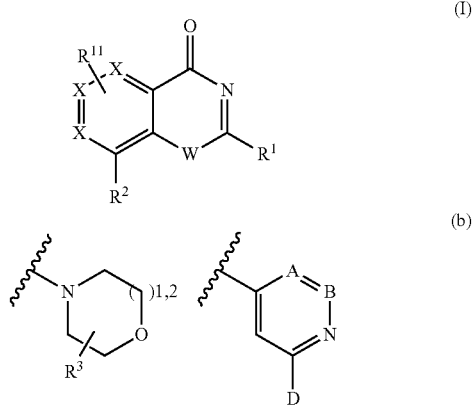

11 Claims, No Drawings

BENZO [E] [1,3] OXAZIN-4-ONE DERIVATIVES AS PHOSPHOINOSITIDE 3-KINASE INHIBITORS

CROSS REFERENCE TO A RELATED APPLICATION

This application is a National Stage Application of International Application Number PCT/GB2010/051221, filed Jul. 23, 2010; which claims priority to Great Britain Application Nos. 0913248.1, filed Jul. 29, 2009 and 0915789.2, filed Sep. 9, 2009; all of which are incorporated herein by reference in their entirety.

FIELD OF THE INVENTION

The present invention relates to novel compounds which act as inhibitors of phosphoinositide 3-kinases (PI3Ks), notably of the class IA subfamily, and therefore have therapeutic utility.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into four distinct subfamilies, named class I, II, III and IV, based upon their substrate specificities. Of these, class IA PI3Ks possess a p110α, p110β, or p110δ catalytic subunit complexed with one of three regulatory subunits, p85α, p85β or p55δ. A single class IB PI3K exists, comprising a p110γ catalytic and a p101 regulatory subunit. Class IA PI3Ks are activated by receptor tyrosine kinases, antigen receptors, G-protein coupled receptors (GPCRs), and cytokine receptors, and the class IB PI3K is activated by GPCRs. The class IA PI3Ks primarily generate phosphatidylinositol-3,4,5-triphosphate (PI(3,4,5)P3), a second messenger that activates the downstream target AKT. The consequences of biological activation of AKT include tumour progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. As such, compounds which are able to modulate PI3K have important therapeutic potential.

WO08/064018 discloses compounds for inhibiting the activity of PI3K-delta.

SUMMARY OF THE INVENTION

The present invention is a compound of formula (I):

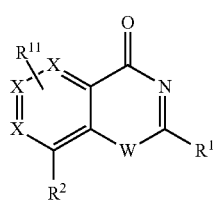

(I)

wherein:

W is O, N—H, N-alkyl, N-alkenyl, N-alkynyl, N-aryl, N-heteroaryl or S;

each X is independently CH or N;

$R^1$ is

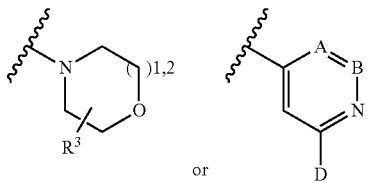

$R^3$ is H, alkyl, $NH_2$, OH, =O or halogen;
each A and B are independently CH or N;
D is $NHR_4$;
$R^4$ is H, alkyl, —C(O)-alkyl, —C(O)—$NH_2$, —C(O)—NH-alkyl, —$SO_2$-alkyl, —$SO_2$—$NH_2$ or —$SO_2$—NH-alkyl;
$R^2$ is aryl substituted with at least one nitrogen-containing group or $R^2$ is a nitrogen-containing heteroaryl, cycloalkyl substituted with a nitrogen-containing group, nitrogen-containing cycloalkyl, $C_1$-$C_6$ mono alkylamino, $C_1$-$C_6$ bis alkylamino, $C_1$-$C_6$ acylamino, $C_1$-$C_6$ aminoalkyl, mono ($C_1$-$C_6$ alkyl)amino $C_1$-$C_6$ alkyl, bis ($C_1$-$C_6$ alkyl)amino $C_1$-$C_6$ alkyl, $C_1$-$C_6$-acylamino or $C_1$-$C_6$ alkynyl-$NR^{11}$;
$R^{11}$ is H, alkyl, alkenyl, alkynyl, aryl, heteroaryl, halogen, O-alkyl, NH-alkyl, N-dialkyl, —C(O)—$R^7$, —C(O)—$NH_2$, —C(O)—NH—$R^7$, —$SO_2$—$R^7$, —$SO_2$—$NH_2$, —$SO_2$—NH—$R^7$, NH-acyl, NH-sulfonyl, $NR^7$-acyl, $NR^7$-sulfonyl, N—C(O)—NH—$R^7$, N—$SO_2$—NH—$R^7$, N—C(O)—$NR^7R^7$ or N—$SO_2$—$NR^7R^7$; and
$R^7$ is alkyl, aryl or heteroaryl.

DESCRIPTION OF THE PREFERRED EMBODIMENTS

As used herein, alkyl means a $C_1$-$C_6$ alkyl group, which can be linear or branched. Preferably, it is a $C_1$-$C_4$ alkyl moiety. Examples include methyl, ethyl, n-propyl and t-butyl.

As used herein, alkenyl means a $C_2$-$C_6$ alkenyl group. Preferably, it is a $C_2$-$C_4$ alkenyl group. It is preferred that the alkenyl radicals a mono- or di-saturated, more preferably monosaturated. Examples include vinyl, allyl, 1-propenyl, isopropenyl and 1-butenyl.

As used herein, alkynyl a $C_2$-$C_6$ alkynyl group which can be linear or branched. Preferably, it is a $C_2$-$C_4$ alkynyl group or moiety. The alkynyl can be optionally substituted.

As used herein, aryl means a monocyclic, bicyclic, or tricyclic monovalent aromatic radical, such as phenyl, biphenyl, naphthyl, anthracenyl, which can be optionally substituted with up to five substituents preferably selected from the $C_1$-$C_6$ alkyl, $C_1$-$C_6$ alkenyl, $C_1$-$C_6$ alkynyl, aryl, heteroaryl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl)amino $C_1$-$C_3$ alkyl, bis($C_1$-$C_3$ alkyl)amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, heteroaryl means a monocyclic, bicyclic or tricyclic monovalent aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents preferably selected from the group of $C_1-C_6$ alkyl, hydroxy, $C_1-C_3$ hydroxyalkyl, $C_1-C_3$ alkoxy, $C_1-C_3$ haloalkoxy, amino, $C_1-C_3$ mono alkylamino, $C_1-C_3$ bis alkylamino, $C_1-C_3$ acylamino, $C_1-C_3$ aminoalkyl, mono ($C_1-C_3$ alkyl)amino $C_1-C_3$ alkyl, bis ($C_1-C_3$ alkyl)amino $C_1-C_3$ alkyl, $C_1-C_3$-acylamino, $C_1-C_3$ alkyl sulfonylamino, halo, nitro, cyano, trifluoromethyl, carboxy, $C_1-C_3$ alkoxycarbonyl, aminocarbonyl, mono $C_1-C_3$ alkyl aminocarbonyl, bis $C_1-C_3$ alkyl aminocarbonyl, —$SO_3H$, $C_1-C_3$ alkylsulphonyl, aminosulfonyl, mono $C_1-C_3$ alkyl aminosulfonyl and bis $C_1-C_3$-alkyl aminosulfonyl.

As used herein, cycloalkyl means a saturated carbocyclic ring, which is 5, 6, or 7-membered. A nitrogen-containing cycloalkyl contains between 1 and 3 nitrogen atoms. The cycloalkyl may be substituted with up to three substituents preferably selected from the group of $C_1-C_6$ alkyl, hydroxy, $C_1-C_3$ hydroxyalkyl, $C_1-C_3$ alkoxy, $C_1-C_3$ haloalkoxy, amino, $C_1-C_3$ mono alkylamino, $C_1-C_3$ bis alkylamino, $C_1-C_3$ acylamino, $C_1-C_3$ aminoalkyl, mono ($C_1-C_3$ alkyl)amino $C_1-C_3$ alkyl, bis ($C_1-C_3$ alkyl)amino $C_1-C_3$ alkyl, $C_1-C_3$-acylamino, $C_1-C_3$ alkyl sulfonylamino, halo, nitro, cyano, trifluoromethyl, carboxy, $C_1-C_3$ alkoxycarbonyl, aminocarbonyl, mono $C_1-C_3$ alkyl aminocarbonyl, bis $C_1-C_3$ alkyl aminocarbonyl, —$SO_3H$, $C_1-C_3$ alkylsulphonyl, aminosulfonyl, mono $C_1-C_3$ alkyl aminosulfonyl and bis $C_1-C_3$-alkyl aminosulfonyl.

As used herein, a nitrogen-containing group is any moiety containing a nitrogen atom. Preferably, the nitrogen-containing group is amino, $C_1-C_6$ mono alkylamino, $C_1-C_6$ bis alkylamino, $C_1-C_6$ acylamino, $C_1-C_6$ aminoalkyl, mono ($C_1-C_6$ alkyl)amino $C_1-C_6$ alkyl, bis($C_1-C_6$ alkyl)amino $C_1-C_6$ alkyl or $C_1-C_6$-acylamino.

In a preferred embodiment, $R^2$ is an aryl substituted with at least one nitrogen-containing group.

More preferably, $R^2$ is an aryl substituted with at least one nitrogen-containing group and at least one halogen.

Preferably, the nitrogen-containing group is amino, $C_1-C_6$ mono alkylamino, $C_1-C_6$ bis alkylamino, $C_1-C_6$ acylamino, $C_1-C_6$ aminoalkyl, mono ($C_1-C_6$ alkyl)amino $C_1-C_6$ alkyl, bis($C_1-C_6$ alkyl)amino $C_1-C_6$ alkyl, $C_1-C_6$-acylamino, $C_1-C_6$ alkynyl-$NR^{11}$ or $NR^6R^6$ wherein each $R^6$ is independently selected from H, alkyl, alkenyl, alkynyl, aryl, heteroaryl, —C(O)—$R^7$, —C(O)—$NH_2$, —C(O)—NH—$R^7$, —$SO_2$—$R^7$, —$SO_2$—$NH_2$, —$SO_2$—NH—$R^7$, N—C(O)—$NR^7R^7$ or N—$SO_2$—$NR^7$ is as defined above.

More preferably, the nitrogen-containing group is amino.

In a further preferred embodiment, $R^2$ is one of the following structures:

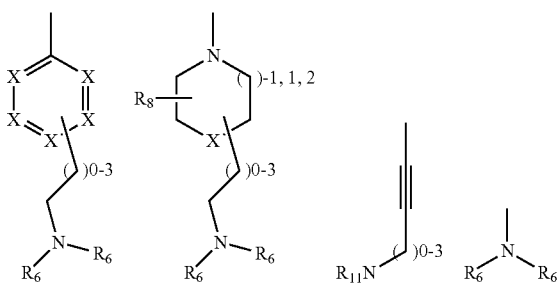

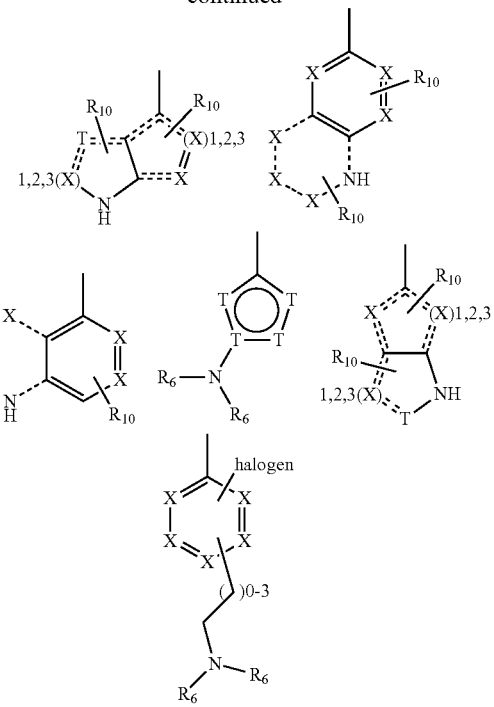

wherein:
$R^{10}$ is H, alkyl, alkenyl, alkynyl, aryl, heteroaryl, $NH_2$, NH—$R^7$, $NR^7R^7$, O—$R^7$, —C(O)—$R^7$, —C(O)$NHR^7$, —$SO_2$—$R^7$, —$SO_2$—$NHR^7$, —NH-acyl, —NH-sulfonyl —$NR^7$-acyl, —$NR^7$-sulfonyl, =O or $SO_2$;

$R^8$ is H, alkyl, alkenyl, alkynyl, aryl, heteroaryl, =O, $SO_2$, —NH—$R^7$, —$NR^7R^7$, O—$R^7$, —C(O)—$NHR^9$, —$SO_2$—$NHR^9$ or —$NR^7$-acyl, —$NR^7$-sulfonyl;

$R^9$ is alkyl, alkenyl, alkynyl, aryl, heteroaryl, $NH_2$, OH, NH—$R^7$, $NR^7R^7$, O—$R^7$, —C(O)—$R^7$, —C(O)$NHR^7$, —$SO_2$—$R^7$, —$SO_2$—$NHR^7$, —NH-acyl, —NH-sulfonyl —$NR^7$-acyl or —$NR^7$- or -sulfonyl;

T is O, N, S or C; and $R^{11}$, $R^7$, $R^6$ and X are as defined above.

Preferably, the halogen is fluorine.

Preferably, $R_1$ is

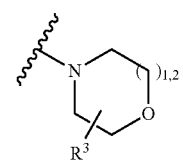

Preferably, W is O.
Preferably, X is CH.
Preferably $R^8$ is H.
Preferably, $R^3$ is H.
Preferably, the compound is of structure A or B, as defined in the Examples.

The compounds defined herein are useful in therapy. Preferably, the therapy is of cancer, cardiovascular disease, immune disorders, an inflammatory disorder or a disease of the endocrine system.

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, salicylic, stearic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sublingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterised by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterised as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

The present invention will now be illustrated by the following examples.

EXAMPLES

Compound A) 8-(4-aminophenyl)-2-morpholino-4H-benzo[e][1,3]oxazin-4-one

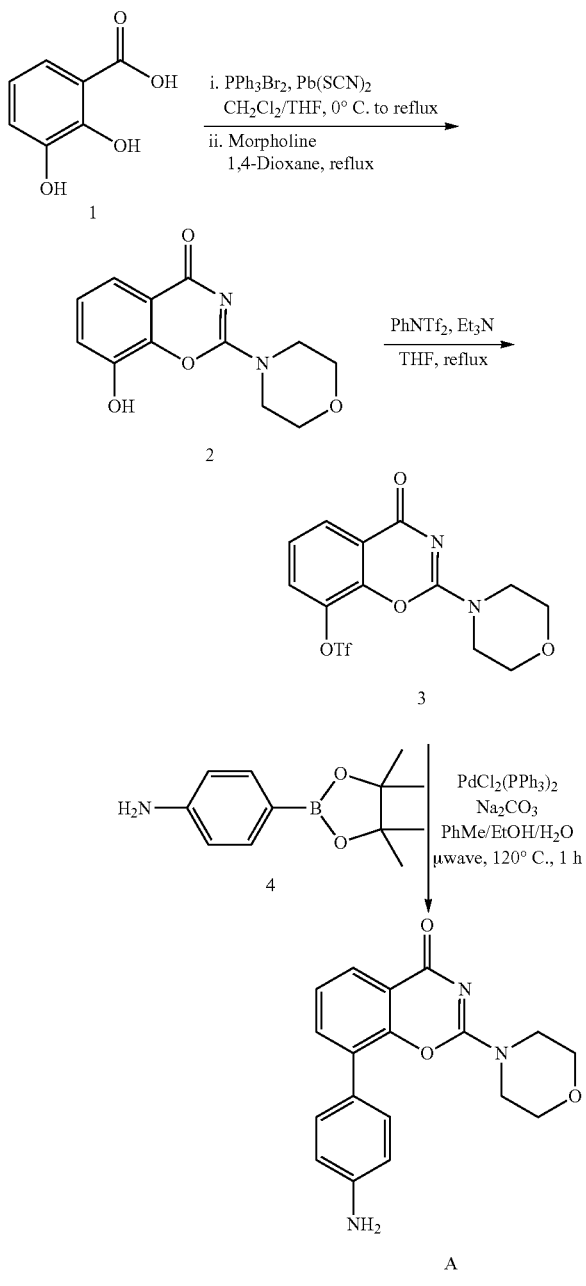

(2): 8-Hydroxy-2-morpholin-4-yl-benzo[e][1,3]oxazin-4-one

To a suspension of Pb(SCN)$_2$ (3.16 g, 9.8 mmol, 1.5 eq) in CH$_2$Cl$_2$ (50 mL) at 0° C. was added dropwise a solution of PPh$_3$Br$_2$ (3.3 g, 7.8 mmol, 1.2 eq) in CH$_2$Cl$_2$ (40 mL) under Ar(g). After 5 min, a solution of 2,3-dihydroxybenzoic acid (1.0 g, 6.5 mmol, 1 eq) in CH$_2$Cl$_2$/THF (40 mL, 4:1) was slowly added, and the mixture was left to warm to rt over 1 h before being refluxed for an additional 3 h. The resulting solution was filtered and the filter cake was washed with CH$_2$Cl$_2$ and hot acetone. The solvent was removed in vacuo to give a pale yellow solid (4.0 g). Dioxane (30 mL) was then added, followed by morpholine (6 mL, 65 mmol, 10 eq). The reaction mixture was refluxed for 4 h. The solvent was then removed in vacuo and the residue was further purified by silica gel column chromatography with CH$_2$Cl$_2$/MeOH (19:1-9:1) to yield 2 as a pale yellow solid (1.53 g, 95%); $^1$H NMR (400 MHz, CDCl$_3$+10% MeOD) δH: 7.35-7.41 (m, 1H), 7.04 (d, J=4.7 Hz, 2H), 3.72-3.79 (m, 4H), 3.64-3.70 (m, 4H). MS (ES$^+$) 271.0 (100%, [M+Na]$^+$).

(3): Trifluoro-methanesulfonic acid 2-morpholin-4-yl-4-oxo-4H-benzo[e][1,3]oxazin-8-yl ester To a solution of 2 (1.43 g, 5.77 mmol, 1 eq) and N-phenyl-triflimide (3.50 g, 9.80 mmol, 1.7 eq) in THF (20 mL) was added Et3N (2.36 mL, 17.3 mmol, 3 eq) under Ar(g). The reaction mixture was refluxed for 4 h, then left to stir at room temperature overnight. The solution was diluted with water (30 mL), and extracted with CH$_2$Cl$_2$ (2×20 mL). The combined organic extracts were dried over MgSO and the solvent was removed in vacuo. The residue was further purified by silica gel column chromatography with CH$_2$Cl$_2$/MeOH (1:0-19:1) to yield 3 as a white solid (1.71 g, 78%); $^1$H NMR (400 MHz, CDCl$_3$) δH: 8.16 (dd, J=7.8, 1.5 Hz, 1H), 7.54 (dd, J=8.2, 1.3 Hz, 1H), 7.42 (t, J=8.0 Hz, 1H), 3.91-3.98 (m, 2H), 3.80-3.88 (m, 6H). MS (ES+) 403.0 (100%, [M+Na]$^+$).

(Compound A): 8-(4-Amino-phenyl)-2-morpholin-4-yl-benzo[e][1,3]oxazin-4-one

A vessel was loaded with 3 (100 mg, 0.26 mmol, 1 eq) followed by 4-(4,4,5,5-etramethyl-[1,3,2]dioxaborolan-2-yl)-phenylamine, 4 (63 mg, 0.29 mmol, 1.1 eq), sodium bicarbonate (83 mg, 0.79 mmol, 3 eq) and PdCl$_2$(PPh$_3$)$_2$ (9.2 mg, 0.01 mmol, 5 mol %). A mixture of PhMe (2 mL), EtOH (1 mL) and H$_2$O (0.5 mL) was added and the system was flushed with Ar. The reaction mixture was then heated in a microwave reactor for 1 h at 120° C. The mixture was partitioned between CH$_2$Cl$_2$ (2×10 mL) and H$_2$O (5 mL). The combined organic extracts were dried over MgSO$_4$ and the solvent was removed in vacuo. The residue was further purified by silica gel column chromatography with CH$_2$Cl$_2$/MeOH (49:1-19:1) to yield the product, A, as a white solid (26 mg, 31%).

$^1$H NMR (400 MHz, CDCl$_3$) δH: 8.08 (dd, J=7.7, 1.7 Hz, 1H), 7.59 (dd, J=7.5, 1.6 Hz, 1H), 7.38 (t, J=7.7 Hz, 1H), 7.31 (d, J=8.5 Hz, 2H), 6.78 (d, J=8.5 Hz, 2H), 3.81-3.96 (m, 4H), 3.68-3.79 (m, 4H), 3.59 (br. s., 2H). MS (ES$^+$) 324.1 (100%, [M+H]$^+$).

Biochemical Data

Compound A displays greater class IA/IB PI3K selectivity compared with industry-standard inhibitor, LY294002, which has the structure

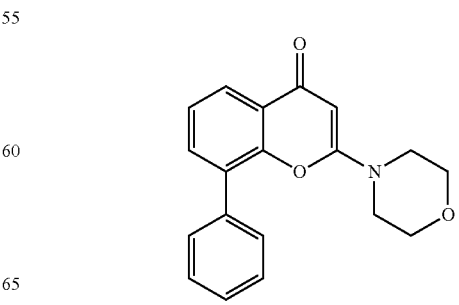

The results are summarised in the table below:

| Cpd/Biochemical Activity | IC50 PI3K-p110β (uM) (Class IA Enzyme) | IC50 PI3K-p110γ (uM) (Class IB Enzyme) |
|---|---|---|
| Compound A | 2.34 | 20.5 |
| LY294002 | 1.70 | 4.11 |

Compound B) 8-(4-Amino-2-fluoro-phenyl)-2-morpholin-4-yl-benzo[e][1,3]oxazin-4-one

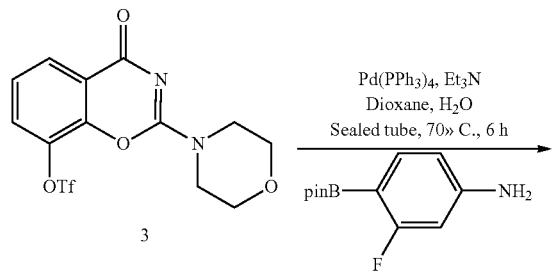

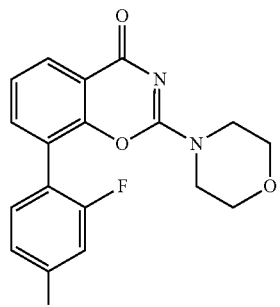

To a mixture of trifluoro-methanesulfonic acid 2-morpholin-4-yl-4-oxo-4H-benzo[e][1,3]oxazin-8-yl ester, 3 (60 mg, 0.16 mmol, 1 eq), 3-fluoro-4-(4,4,5,5-tetramethyl-[1,3,2]dioxaborolan-2-yl)-phenylamine (47 mg, 0.20 mmol, 1.3 eq), Pd(PPh₃)₄ (7.6 mg, 0.007 mmol, 5 mol %) in dioxane (2 mL) and H₂O (1mL) was added Et₃N (66 mL, 0.48 mmol, 3 eq) dropwise. The reaction mixture was heated up in a pressure tube at 70° C. for 6 h. Upon cooling, the solution was partitioned between EtOAc (15 mL) and H₂O (10 mL). The aqueous layer was further extracted with EtOAc (2×5 mL) and DCM (5 mL). The combined organic extracts were dried over MgSO₄ and the solvent was removed in vacuuo. The residue was further purified by silica gel column chromatography with EtOAc:MeOH (1:0-13:1) to yield the product, B, as a pale brown solid (47 mg, 87%). ¹HNMR (400 MHz, CDCl₃+ 10% MeOD) $\delta_H$: 7.98 (dd, J=7.5, 1.5 Hz, 1H), 7.62 (dd, 1.5 Hz, 1H), 7.42 (t, J=7.5 Hz, 1H), 7.12 (t, J=8.3 Hz, 1H), 6.59 (dd, J=8.3, 2.3 Hz, 1H), 6.52 (dd, J=12.5, 2.0 Hz, 1H), 3.49-3.90 (m, 10H). MS (ES⁺) 342.1 (100%, [M+H]⁺).

Biochemical Data

Compound B displays selectivity for PI3K-p110β. The results are summarised in the table below:

| Cpd/Biochemical Activity | IC$_{50}$ PI3K-p110 α (uM) | IC$_{50}$ PI3K-p110β (uM) | IC$_{50}$ PI3K-p110δ (uM) | IC$_{50}$ PI3K-p110γ (uM) |
|---|---|---|---|---|
| Compound B | 3.406 | 0.538 | 1.69 | 17.780 |

The invention claimed is:
1. A compound of formula (I):

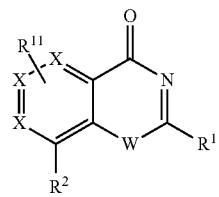

wherein:
W is O;
each X is independently CH or N;
R¹ is

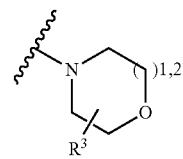

R³ is H, alkyl, NH₂, OH, =O or halogen;
R² is aryl substituted with at least one nitrogen-containing group or R² is a nitrogen-containing heteroaryl, cycloalkyl substituted with a nitrogen-containing group, nitrogen-containing cycloalkyl, C₁-C₆ mono alkylamino, C₁-C₆ bis alkylamino, C₁-C₆ acylamino, C₁-C₆ aminoalkyl, mono (C₁-C₆ alkyl)amino C₁-C₆ alkyl, bis (C₁-C₆ alkyl)amino C₁-C₆ alkyl, C₁-C₆-acylamino or C₁-C₆ alkynyl-NR¹¹; wherein the nitrogen-containing group is amino, C₁-C₆ mono alkylamino, C₁-C₆ bis alkylamino, C₁-C₆ acylamino, C₁-C₆ aminoalkyl, mono (C₁-C₆ alkyl)amino C₁-C₆ alkyl, bis(C₁-C₆ alkyl)amino C₁-C₆ alkyl, C₁-C₆-acylamino, alkynyl-NR¹¹ or NR⁶R⁶ wherein each R⁶ is independently selected from H, alkyl, alkenyl, alkynyl, aryl, heteroaryl, —C(O)—R⁷, —C(O)—NH₂, —C(O)—NH—R⁷, —SO₂—R⁷, —SO₂—NH₂, —SO₂—NH—R⁷, N—C(O)—NR⁷R⁷ or N—SO₂—NR⁷ R⁷;
R¹¹ is H; and
R⁷ is alkyl, aryl or heteroaryl.
2. The compound according to claim 1, wherein R² is an aryl substituted with at least one nitrogen-containing group, wherein the nitrogen-containing group is as defined in claim 1.
3. The compound according to claim 1, wherein R² is an aryl substituted with at least one nitrogen-containing group and at least one halogen, wherein the nitrogen-containing group is as defined in claim 1.
4. The compound according to claim 1, wherein the nitrogen-containing group is amino.

5. A compound according to claim 1, wherein: $R^2$ is

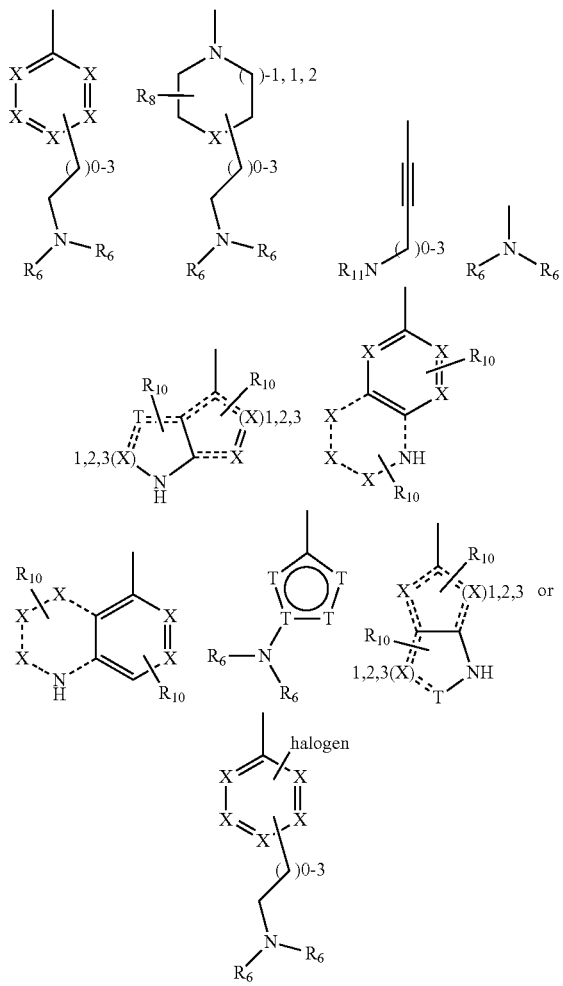

wherein:
$R^{10}$ is H, alkyl, alkenyl, alkynyl, aryl, heteroaryl, NH$_2$, NH—R$^7$, NR$^7$R$^7$, O—R$^7$, —C(O)—R$^7$, C(O)NHR$^7$, —SO$_2$—R$^7$, —SO$_2$—NHR$^7$, —NH-acyl, —NH-sulfonyl —NR$^7$-acyl, —NR$^7$-sulfonyl, =O or SO$_2$;
$R^8$ is H, alkyl, alkenyl, alkynyl, aryl, heteroaryl, =O, SO$_2$, —NR$^7$R$^7$, O—R$^7$, —C(O)—NHR$^9$, —SO$_2$—NHR$^9$ or —NR$^7$-acyl, —NR$^7$-sulfonyl;
$R^9$ is alkyl, alkenyl, alkynyl, aryl, heteroaryl, NH$_2$, OH, NH—R$^7$, NR$^7$R$^7$, O—R$^7$, —C(O)—R$^7$, —C(O)NHR$^7$, —SO$_2$—R$^7$, —SO$_2$—NHR$^7$, —NH-acyl, —NH-sulfonyl —NR$^7$-acyl or —NR$^7$ or -sulfonyl; and
T is O, N, S or C.

6. The compound according to claim 1, wherein the halogen is fluorine.

7. The compound according to claim 1, wherein X is CH.

8. The compound according to claim 1, wherein $R^8$ is H.

9. The compound according to claim 1, which has the following structure:

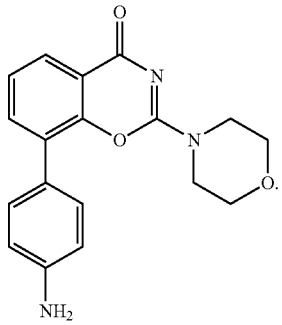 [SMILES: Nc1ccc(-c2cccc3c(=O)nc(N4CCOCC4)oc23)cc1]

10. The compound according to claim 1, which has the following structure:

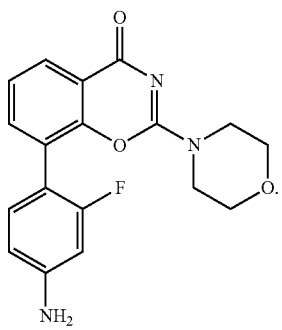 [SMILES: Nc1ccc(-c2cccc3c(=O)nc(N4CCOCC4)oc23)c(F)c1]

11. A method for treating rheumatoid arthritis wherein said method comprises administering, to a subject in need of such treatment, an effective amount of a compound of claim 1.

* * * * *

UNITED STATES PATENT AND TRADEMARK OFFICE
CERTIFICATE OF CORRECTION

PATENT NO. : 8,981,087 B2  
APPLICATION NO. : 13/384310  
DATED : March 17, 2015  
INVENTOR(S) : Stephen Joseph Shuttleworth et al.

Page 1 of 1

It is certified that error appears in the above-identified patent and that said Letters Patent is hereby corrected as shown below:

In the Claims

Column 12,  
Line 50, "$C_1$-$C_6$-acylamino, alkynyl-$NR^{11}$" should read --$C_1$-$C_6$-acylamino, $C_1$-$C_6$ alkynyl-$NR^{11}$--.

Column 13,  
Lines 48-49, "O, $SO_2$, —$NR^7R^7$," should read --O, $SO_2$, -NH-$R^7$, -$NR^7R^7$,--.

Signed and Sealed this  
Seventh Day of July, 2015

Michelle K. Lee  
*Director of the United States Patent and Trademark Office*